United States Patent
Hirata et al.

(10) Patent No.: US 7,118,684 B2
(45) Date of Patent: *Oct. 10, 2006

(54) TREATMENT OF FIBER WITH WATER CONTAINING FINE POWDER OF NOBLE METAL DISPERSED THEREIN

(75) Inventors: Yoshihiro Hirata, Kyoto (JP); Yoshio Ueda, Kyoto (JP); Hiroaki Takase, Kyoto (JP); Kazuaki Suzuki, Kyoto (JP)

(73) Assignee: Phild Co., Ltd., Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/492,247

(22) PCT Filed: Oct. 11, 2002

(86) PCT No.: PCT/JP02/10565

§ 371 (c)(1),
(2), (4) Date: Jul. 6, 2004

(87) PCT Pub. No.: WO03/033809

PCT Pub. Date: Apr. 24, 2003

(65) Prior Publication Data

US 2004/0244120 A1    Dec. 9, 2004

(30) Foreign Application Priority Data

Oct. 12, 2001  (JP) ............................ 2001-315171

(51) Int. Cl.
 *D06M 11/83*  (2006.01)
(52) U.S. Cl. .................... 252/8.91; 252/8.81
(58) Field of Classification Search ............... 8/115.51, 8/495; 442/6, 31, 59, 136, 327; 252/8.91, 252/8.81
See application file for complete search history.

(56) References Cited

U.S. PATENT DOCUMENTS

| | | | | |
|---|---|---|---|---|
| 4,313,734 A | * | 2/1982 | Leuvering .................. 436/525 |
| 5,106,533 A | * | 4/1992 | Hendrickson et al. ... 106/31.65 |
| 5,876,480 A | * | 3/1999 | Markowitz et al. ........... 75/252 |
| 6,136,044 A | * | 10/2000 | Todd .............................. 8/495 |
| 6,245,494 B1 | * | 6/2001 | Andriessen et al. ........ 430/346 |
| 6,569,359 B1 | * | 5/2003 | Yukinobu et al. ............ 252/514 |
| 6,689,190 B1 | * | 2/2004 | Pozarnsky ..................... 75/332 |
| 6,780,475 B1 | * | 8/2004 | Fulton et al. ................ 427/458 |
| 6,869,626 B1 | * | 3/2005 | Hirata et al. .................. 426/66 |
| 2004/0213995 A1 | | 10/2004 | Hirata et al. |

FOREIGN PATENT DOCUMENTS

| | | | |
|---|---|---|---|
| EP | 0 672 450 A1 | | 9/1995 |
| EP | 0672450 | * | 9/1995 |
| JP | 54-82500 | | 6/1979 |
| JP | 62-299587 | | 12/1987 |
| JP | 03-42032 | | 2/1991 |
| JP | 404018178 A | * | 1/1992 |
| JP | 05-155629 | | 6/1993 |
| JP | 6-21425 | * | 3/1994 |
| JP | 07-173511 | | 7/1995 |
| JP | 2876083 | * | 3/1999 |
| JP | 2002-020969 | | 1/2002 |
| JP | 2002-045684 | | 2/2002 |
| JP | 2002-528369 | | 9/2002 |
| WO | WO 98/42909 | | 10/1998 |
| WO | WO 98/53132 | | 11/1998 |
| WO | WO 01/17479 A2 | | 3/2001 |
| WO | WO 02/02860 | | 1/2002 |

OTHER PUBLICATIONS

Japio English language trnslation of JP 2876083, Mar. 1999.*
STN abstract of JP 2876083, Mar. 1999.*
Japio English language translation of JP 6-21425 Mar. 1994.*
STN abstract of JP 6-21425, Mar. 1994.*
Japio English language translation of JP 2876084 Mar. 1999.*
STN abstract of JP 2876084, Mar. 1999.*
U.S. Appl. No. 10/130,123, filed Aug. 27, 2002, Hirata et al.
U.S. Appl. No. 10/468,110, filed Dec. 15, 2003, Hirata et al.
U.S. Appl. No. 10/472,702, filed Feb. 19, 2004, Hirata et al.
U.S. Appl. No. 10/473,181, filed Jan. 12, 2004, Hirata et al.

* cited by examiner

*Primary Examiner*—Lorna M. Douyon
*Assistant Examiner*—Amina Khan
(74) *Attorney, Agent, or Firm*—Knobbe, Martens, Olson & Bear LLP

(57) ABSTRACT

Burn noble metal in high-pressure water using hydrogen and oxygen to produce noble metal micro-dispersion water in which super-fine noble metal particles are dispersed, and use the obtained noble metal micro-dispersion water to treat fiber products in order to provide high-function fiber products, typically clothes, which offer excellent health-promoting function and cleanliness-improving function.

3 Claims, 2 Drawing Sheets

TREATMENT OF FIBER WITH WATER CONTAINING FINE POWDER OF NOBLE METAL DISPERSED THEREIN

This application is the U.S. National Phase under 35 U.S.C. §371 of International Application PCT/JP02/10565, filed on Oct. 11, 2002, which claims priority of Japanese Patent Application No. 2001-315171 filed on Oct. 12, 2001. The International Application was published under PCT Article 21(2) in a language other than English.

FIELD OF THE INVENTION

This invention relates to fiber treatment using noble metal micro-dispersion water. Specifically, the invention relates to a fiber treatment agent comprising noble metal micro-dispersion water, a method for treating fiber using such treatment agent, and a high-function fiber material or product obtained through treatment using such treatment agent.

DESCRIPTION OF THE RELATED ART

Reflecting the growing trend toward healthier and cleaner lifestyle choices, products that offer benefits in promoting health or improving cleanliness are drawing the attention. In particular, demands and requests for these products are increasing in the areas of food, clothes, daily necessities, etc. Among others, clothes (fiber products) are always worn on our body, and accordingly there are strong consumer demands for clothes that can effectively promote heath, prevent diseases or improve cleanliness.

Against this backdrop, healthy clothes have been actively studied and many products have been developed to date. For example, clothes offering disease-curing effects are commercially available, which utilize fiber material or carbon fiber that generates far infrared rays or magnetism. At the same time, tormarine-based fiber products claiming a fatigue-relief effect and clean, antibacterial fiber products utilizing inorganic compounds, chitosan, etc., are also generating interest.

However, many of these commercial products are yet to offer satisfactory levels of health-promoting function or cleanliness-improving efficacy or even the basic clothing function, and the aforementioned consumer demands are not fully answered yet.

On the other hand, noble metals, especially gold, have been considered some of the most valuable materials available to men since the ancient times and used primarily in ornaments and treasures. In recent years, gold has been found to promote human health and improve cleanliness and is used in such applications as pure-gold health bracelet or Japanese sake containing gold foil. Of late, silver compounds are also used in commercial products as an antibacterial agent that improves cleanliness.

However, the health benefits of these health products have not been fully recognized, despite their very pricey nature due to use of pure gold, etc.

In recent years, the health functions of noble metals have been again drawing the attention of the increasingly health-conscious public. In particular, gold ion and fine gold particles are now known to offer more remarkable health-promoting function than gold metal itself or gold foil.

Among all noble metals, gold in the form of gold ion or fine gold particle is generating interest as a material potentially offering health-promoting function and disease-curing effect, and technologies to harness these possibilities of gold are eagerly awaited. The basic application modes of gold include aqueous solution or water dispersion containing gold ions and fine gold particles. However, several problems must be solved before they can be put to practical use.

For example, it is difficult to dissolve gold ions and fine gold particles in water, and the only methods available before were those that simply mix gold foil or powder with water or use gold electrolyte. However, these conventional methods couldn't produce desired products economically and the final products didn't provide sufficient health-promoting function because gold remained in foil or powder form. Additionally, safety of gold foil or chemical electrolyte of gold in the human body is not yet confirmed. These industrial and technical problems still remain unresolved.

Research and development efforts are underway in this technical field in order to solve these problems and embody the potential health-promoting function and disease-curing effect of gold ion and fine gold particle. However, to date only a few technologies have been reported in this field, where many developments should be expected in the future.

Only a small number of representative technologies have been published as unexamined patent applications. They include an antibacterial beverage tank containing an inorganic antibacterial agent produced by fixing gold ions or other metal ions offering antibacterial effect to zeolite ion-exchange material (Registered Japanese Utility Model No. 3046284), a production of mineral water that contains gold ions and other minerals beneficial to the human body, wherein such mineral water is produced by setting a mineral carrier in water and causing it to release gold ions, etc., through addition of acid, electrolysis, or other method (Japanese Patent Application Laid-open No. 9-220580), and a production of sterilizing antiseptic water that offers excellent sterilizing effect at low cost, wherein such antiseptic water is produced by dissolving gold or other heavy metal in oxidation potential water (Japanese Patent Application Laid-open No. 9-10772).

As explained above, there are strong consumer demands for the development of high-function fiber products, mainly in the form of clothes, which offer excellent health-promoting function and cleanliness-improving function. On the other hand, in light of their potential as a functional material in the areas of health promotion and cleanliness improvement, noble metal materials may be utilized in the development of fiber products offering excellent health-promoting function and cleanliness-improving function. However, practical technologies are not yet reported at the present.

When the existing publications of unexamined patent applications are studied, those relating to utilization of noble metal materials in fiber products are limited to a few involving coloring or dying of fiber materials and production of ornaments using fiber materials.

DISCLOSURE OF THE INVENTION

As explained above, development of better fiber products is desired for promotion of health and improvement of cleanliness. On the other hand, noble metal materials have been found to offer potential utility as a functional material that can promote health and improve cleanliness. However, utilization of noble metal materials is difficult in actuality and there are expectations for the development of simple and economical technologies that can demonstrate high health-promoting function and cleanliness-improving function.

In view of the above situation, the present invention aims to embody technology to utilize noble metal materials and allow use of the technology in the development of fiber products offering excellent health-promoting function and cleanliness-improving function, while solving at the same time the aforementioned problems associated with fiber products and noble metal materials.

By solving the aforementioned problems, the present invention contributes to the development of fiber products offering excellent health-promoting function and cleanliness-improving function and also to the advancement of future technological development and application regarding the utility of ions and fine particles of noble metal materials.

The basic modes of applying noble metal materials as proposed by the current technologies are aqueous solution or water dispersion of ions and fine particles. However, commercialization of these applications is hindered by several problems that must be solved. For example, it is difficult to dissolve noble metal ions and fine particles in water, and the only methods available before were those that simply mix gold foil or powder with water or use gold electrolyte. However, these conventional methods couldn't produce desired products economically and the final products didn't provide sufficient health-promoting function.

To address this condition, the present invention applies noble metal materials in the form of micro-dispersion water. To achieve micro-dispersion water of noble metal material the present invention utilizes the invention described in "Method and Apparatus for Producing Aqueous Solution of Super-Fine Gold Particles" (Japanese Patent Application No. 11-327653), a pending patent earlier filed by the same applicants.

The present invention treats fiber using a fiber treatment agent comprising micro-dispersion water in which super-fine noble metal particles are dispersed, and utilizes a special method to obtain micro-dispersion water of noble metal material.

The basic structure of the present invention comprising (1) through (4) below, and includes all other applications based own this basic structure:

(1) A fiber treatment agent comprising micro-dispersion water in which super-fine noble metal particles are dispersed.

(2) A method for treating fiber, wherein fiber is treated using a fiber treatment agent comprising micro-dispersion water in which super-fine noble metal particles are dispersed.

(3) A fiber material or product that contains super-fine noble metal particles or has the particles externally attached on it, as obtained through treatment using a fiber treatment agent comprising micro-dispersion water in which super-fine noble metal particles are dispersed.

(4) A fiber product described in (3), wherein the fiber product is a product selected from among panty hoses, socks, gloves, undergarment, shirt, bedding, healthy athletic garment, muffler, towel, supporter and wristband.

Components (1) through (4) of the present invention are explained in detail by referring to the drawings.

Invention component (1) refers to a fiber treatment agent comprising micro-dispersion water in which super-fine noble metal particles are dispersed, and provides the basis for invention components (2) through (4). It offers a new treatment agent that adds the health function, antibacterial function and other unique functions of noble metals.

After studying new ways to produce fine powder (fine particles) of titanium metal, which is considered an important high-function metal and whose importance is likely to grow further, the inventors developed and filed a patent application for a method and apparatus for embodying a simple, efficient and economical production of fine titanium powder offering very high purity and comprising uniform particle shape and size. The present invention can be applied to metals other than titanium, such as germanium, zirconium and tin, and the method under the present invention has actually been put to commercial applications for, simple and economical production of fine powder of noble metals such as gold, silver or platinum or dispersion of such fine noble metal powder.

Before, it was impossible to dissolve fine noble metal particles in water, and techniques to disperse them in water only achieved a limited level of dispersibility. However, the method under the present invention provides an efficient way to produce dispersion of fine noble metal powder offering very high purity and comprising uniform particle shape and size. Such fine powder (fine particles) should be called "super-fine particles" because their particle size is far smaller than normal particles comprising fine powder. One feature of the present invention is to utilize super-fine noble metals particles that have a size of micron to nano-order scale and therefore are much smaller than fine noble metal particles. For this reason, the present invention offers far better dispersibility of particles as well as far more desirable health-promoting efficacy and other benefits of noble metals. In the context of the present invention, "micro-dispersion water" refers to an aqueous solution in which the newly developed "super-fine particles" as mentioned above are dispersed.

On the other hand, among other noble metals gold and silver have been considered two of the most valuable materials available to men since the ancient times and used chiefly in ornaments and treasures. In recent years, their benefits in promoting human health and improving cleanliness have been recognized. In particular, the health benefits of noble metals are drawing the attention of late by reflecting the demands of today's increasingly health-conscious society, and commercial products are now available such as an antibacterial material made by fixing gold ions to zeolite or healthy mineral water containing gold ions.

As the health-promoting function and disease-curing efficacy of noble metals come to be known, there are expectations for further technological development to harness such benefits of noble metals. In addition, although it is known that noble metals in ion or fine particle form yield more remarkable health-promoting function compared with when these metals are used directly or in foil form, no commercial applications are available yet that offer a health-promoting aqueous solution or water dispersion containing noble metal ions or fine particles.

The mechanisms as to why the noble metal materials obtained by the present invention offer health-promoting function and disease-curing efficacy, as well as the details of bioactivity embodied by such materials, are not yet clear. Studies are being conducted to uncover these mechanisms and bioactivity.

After studying ways to commercially apply these health-promoting function and disease-curing efficacy of noble metals and develop the application into a new, effective technology, the inventors conceptualized that the unique functions of noble metals could be effectively put to commercial use by utilizing the method for producing aqueous solution of super-fine gold particles (Japanese Patent Application No. 11-327653), a pending patent filed earlier by the inventors. Additionally, the inventors thought that embodying these functions in fiber products such as clothes would fully answer the consumer's needs for health promotion and cleanliness improvement as mentioned earlier. This thinking led to the development of the present invention.

Component (1) of the present invention is explained in details below.

The present invention mainly comprising micro-dispersion water in which super-fine particles of gold, silver, platinum or other noble metal are micro-dispersed. This micro-dispersion water is produced by the method developed by the inventors for producing a dispersion of super-fine noble metal particles, as explained below.

This method basically burns a mixture gas of oxygen and hydrogen in high-pressure water and heats noble metal material using the resulting combustion gas, thereby producing a dispersion of super-fine noble metal particles. To completely eliminate generation of impurities, a mixture gas of oxygen and hydrogen is burned in water and the water is compressed to high pressures to achieve underwater combustion of the mixture gas. To implement this method, an apparatus for producing dispersion water of super-fine noble metal particles is used, which comprising a pressure-resistant container equipped with a high-pressure water tank, an injection nozzle for oxygen and hydrogen mixture gas, an implement for feeding noble metal material, an ignition plug, and a combustion chamber.

The process and apparatus proposed by this production method is explained using "FIG. 1" and "FIG. 2."

FIG. 1 is a flow chart of the production process of dispersion water of super-fine noble metal particles used in the present invention, while FIG. 2 gives a schematic drawing illustrating the apparatus for producing dispersion water of super-fine noble metal particles used in the present invention.

In the figure, 1 is a production apparatus for dispersion water of super-fine noble metal particles, 2 is a high-pressure water tank (pressure tank), 3 is raw high-pressure water, 4 is dispersed fine noble metal particle, 5 is a combustion-gas injection nozzle, 6 is combustion gas, 7 is a combustion chamber, 8 is a raw water inlet, 9 is a hydrogen feed line, 10 is an oxygen feed line, 11 is an agitator, 12 is an ignition plug, 13 is a discharge pump, 14 is a filter, and 15 is an outlet line for micro-dispersion water product. A water electrolysis mechanism, which is 16, may be attached as an adjunct for production of oxygen and hydrogen mixture gas, wherein 17 is an electrolytic container, 18 is electrolytic water, 19 is an electrode, and 20 is a power supply. Additionally, 21 represents noble metal material, while 22 is an implement for feeding noble metal material.

In this production method, purified raw water such as distilled water is introduced from the water inlet (8) into the pressure tank (2) and compressed to high pressures to produce high-pressure water (3), while noble metal material (21) is fed from the implement for feeding previous metal (22), such as a cylinder. Hydrogen and oxygen are then fed under high pressure, and after further pressurization via a gas pump (P) the two gases are injected as a mixture combustion gas (6) from the nozzle (5). The injected gas is ignited by the ignition plug (12) in the combustion chamber (7) and burned completely to achieve a state of complete steam gas combustion at ultra-high temperature. Noble metal instantly melts in this combustion gas and disperses in water. The dispersion water is agitated and mixed by the agitator (11) driven by an electric motor (M). At this time, super-fine particles of noble metal (4), which have a very small particle size of micron to nano-order scale, are generated. These super-fine particles seem dissolved, rather than dispersed, in water, and a small portion of them is actually dissolved in water.

Underwater combustion provides the most efficient and stable mode for burning hydrogen and oxygen mixture gas, and high pressure is needed to achieve stable combustion.

The physicochemical reason why noble metal material dissolves instantly in combustion gas in high-pressure water and becomes super-fine particles is being studied.

Thus obtained micro-dispersion water is fed by the pump (13) through the filter housing (14) and delivered as product. When filtered through an appropriate filter (14) for a desired purpose, the dispersion water is cleared of the remaining noble metal material and a trace amount of fine noble metal particles that are larger than super-fine particles. This way, refined dispersion water, in which only super-fine particles are dispersed with a portion of them dissolved, can be obtained. Filtered noble metal material and fine noble metal particles can be backwashed and reused to increase cost effectiveness. As for the filter, micron-order hollow-fiber membrane is more desirable than ion-exchange membrane or reverse-osmosis membrane, in order to filter only super-fine particles through.

The noble metal material to be fed should ideally be a bar, but it can also have the shape of sheet, metal foil or particle.

Thus produced noble metal dispersion water is utilized as a material for the fiber treatment agent described in component (1) of the present invention. The generated super-fine noble metal particles have a very strong hydrophobic property and therefore are dispersed in water in a stable manner. They will remain dispersed stably for a long period of time without coagulating, settling or otherwise separating from water.

These super-fine particles are expected to provide health-promoting function or disease-curing efficacy because of their ion-releasing action, very large active surface area, unique properties of each noble metal itself, and fine interaction with water molecules. Little theoretical explanations have been offered to date as to the bioactive functions of super-fine noble metal particles in the human body, such as their health-promoting function and disease-curing efficacy. However, it is assumed that super-fine particles contact the skin directly and activate the human cells, or stimulate the biological acupuncture points in key areas of the human body to promote the metabolism of muscles and cleansing of blood.

The volumes of hydrogen and oxygen gases must be controlled accurately to a ratio of two to one. The reaction time and amount of fuel gas to be burned must also be controlled, because a shorter reaction time will not produce dispersion water offering desired effects, while an excessively longer reaction time will result in over-dispersion and higher cost.

As a specific example, to produce one ton of dispersion water the mixture gas should be injected for around two hours at a rate of around five liters per minute. An excessive gas pressure may damage the apparatus, while an insufficient pressure will allow the gas to flow upward from the nozzle, thereby causing the heated micro-pieces of noble metal material to be wrapped up in air bubbles and diffuse out of water, which will hinder effective generation of super-fine noble metal particles. A desirable atmospheric pressure is around 3.5 atmospheres. The pressure of the high-pressure water in the pressure tank should be around 2 atmospheres.

In this apparatus, it is more advantageous to attach an electrolysis mechanism (16) as an adjunct and use the hydrogen and oxygen obtained by this mechanism. Hydrogen and oxygen supplied from water electrolysis are pure gases and have the volume ratio for ideal combustion (2:1). Water electrolysis also provides an easy way to supply hydrogen and oxygen.

The electrolysis mechanism (16) may use a normal apparatus designed for such purpose, comprising a container (17) that stores electrolytic water (18) and an electrolytic electrode (19). The electrode is connected to a power supply (20). Acid or alkali raw water is electrolyzed to generate oxygen gas at the anode and hydrogen gas at the cathode, which are then supplied as material gases for causing combustion.

The application of the fiber treatment agent proposed by component (1) of the present invention, which aims at embodying the unique functions of noble metals, encompasses fiber materials and products. They include base fiber materials such as short fibers and long fibers, fiber materials such as woven fabrics and non-woven fabrics, and fiber products such as various clothes and beddings.

Fiber materials may be natural fibers such as cotton and silk, semi-synthetic fibers such as rayon and acetate, and synthetic fibers such as polyester fibers, polyamide fibers and acrylic fibers.

Representative fiber products include clothing article used in daily use such as panty hoses, socks, gloves, undergarments, shirts, beddings such as sheets and pajamas, healthy athletic garments, mufflers, supporters and wristbands, and towels and handkerchiefs. In particular, the present invention is effective in the treatment of fibers for use in panty hoses, socks and undergarments, since they contact the skin directly and constantly.

The fiber treatment agent provided by component (1) of the present invention uses dispersion water of super-fine noble metal particles as obtained by the aforementioned production method. The obtained product may be used directly as, or diluted or condensed as appropriate into, a treatment agent.

It is assumed that the bioactive functions exhibited by super-fine noble metal particles in the human body, such as health-promoting function and disease-curing efficacy, are embodied as the super-fine particles contact the skin directly and activate the human cells, or stimulate the biological acupuncture points in key areas of the human body to promote the metabolism of muscles and cleansing of blood. In reality, super-fine noble metal particles have been shown to be effective in promoting perspiration, relieving fatigue, increasing energy level, enhancing stamina, increasing appetite, lowering blood pressure, and so on.

Component (2) of the present invention provides a method for treating fiber, wherein fiber is treated using a fiber treatment agent comprising micro-dispersion water in which super-fine noble metal particles are dispersed. As for the means of treatment, impregnation, attachment, mixing, etc., may be adopted as deemed appropriate.

Under the impregnation treatment method, fiber material, clothing, etc., is soaked in micro-dispersion water of super-fine noble metal particles, after which the material is wrung and dried as necessary.

Under the attachment treatment method, micro-dispersion water of super-fine noble metal particles is directly applied or sprayed onto fiber material, clothing, etc., after which the material is dried as necessary.

Under the mixing treatment method, micro-dispersion water of super-fine noble metal particles is mixed with the processing solution, etc., in the production process of fiber material, so as to allow the super-fine particles to mix into the microstructure of the fiber itself.

Component (3) of the present invention provides a fiber material or product that contains super-fine noble metal particles or has the particles externally attached on it, wherein such fiber material/product is obtained through treatment using a fiber treatment agent comprising micro-dispersion water in which super-fine noble metal particles are dispersed, while component (4) of the present invention relates to a fiber product obtained through treatment using a fiber treatment agent comprising micro-dispersion water in which super-fine noble metal particles are dispersed, typically embodied as panty hoses, socks, gloves, undergarment, shirt, bedding, healthy athletic garment, muffler, towel, supporter or wristband.

Attachment of super-fine noble metal particles on fiber products obtained by the present invention has been confirmed on enlarged electron microscope photographs. The particles are attached/fixed firmly and they are rarely removed by normal washing. This is probably because the micro-protrusion structure near fiber surface is wrapping and thus protecting the fine particles.

DESCRIPTION OF THE SYMBOLS

| | |
|---|---|
| 1: Apparatus for producing dispersion water of super-fine noble metal particles | 2: Pressure tank |
| 3: Pressurized water | 4: Fine noble metal particles |
| 5: Injection nozzle | 6: Mixture gas |
| 7: Combustion chamber | 8: Inlet for pressurized water |
| 9: Hydrogen feed line | 10: Oxygen feed line |
| 11: Agitator | 12: Ignition plug |
| 13: Pump | 14: Filter |
| 15: Product delivery line | 16: Electrolysis mechanism |
| 17: Electrolytic container | 18: Electrolytic water |
| 19: Electrode | 20: Power supply |
| 21: Noble metal material | 22: Implement for feeding noble metal material |

BEST MODE FOR CARRYING OUT THE INVENTION

Examples of the present invention are explained according to the drawings. Note, however, that the present invention is not limited to these examples.

EXAMPLE 1

Figure 1:
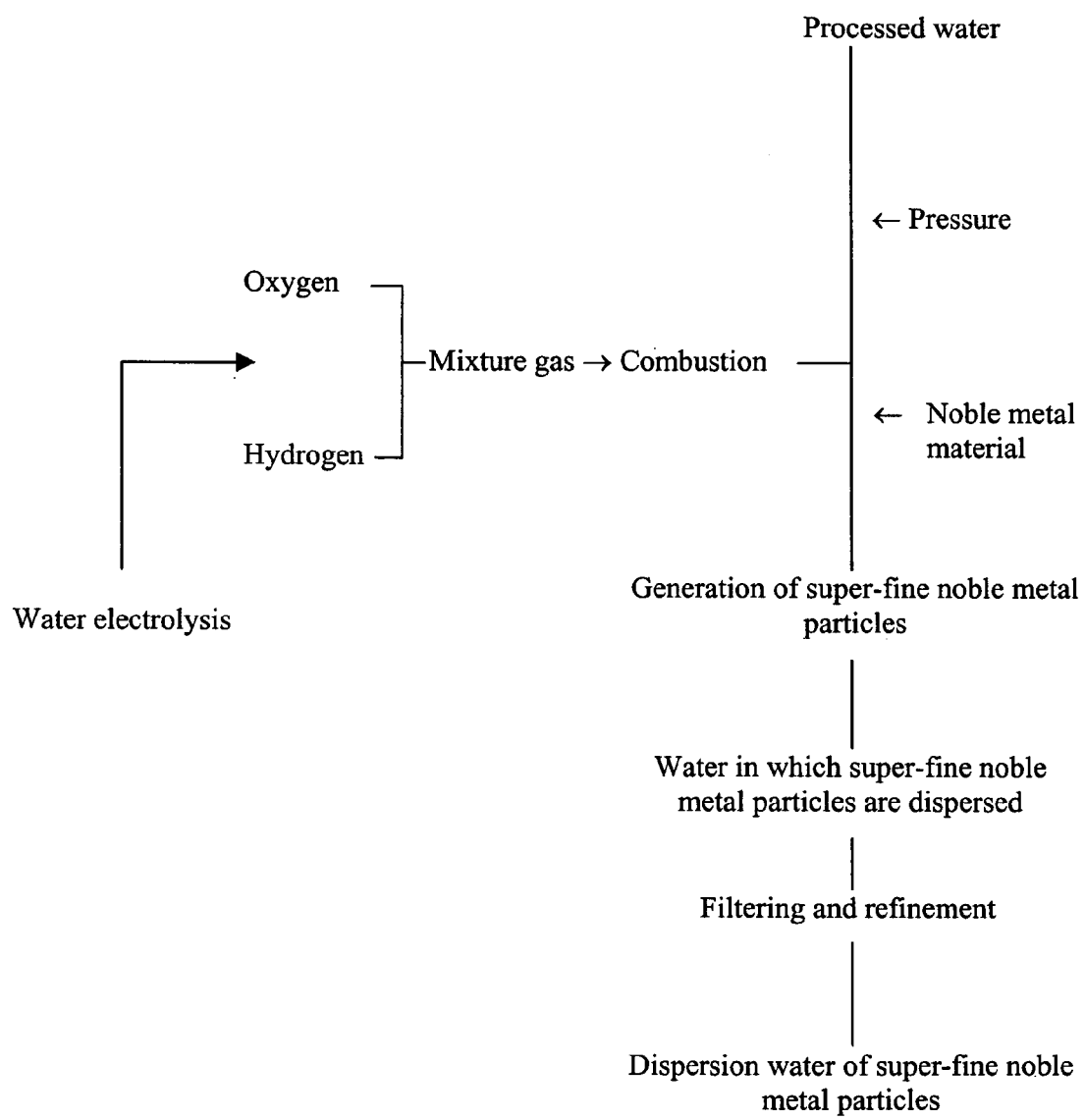
"FIG. 1"
A flow chart outlining the process for producing dispersion water of super-fine noble metal particles as proposed by the present invention "FIG. 2"
A schematic drawing illustrating the apparatus for producing dispersion water of super-fine noble metal particles as proposed by the present invention
Figure 2:
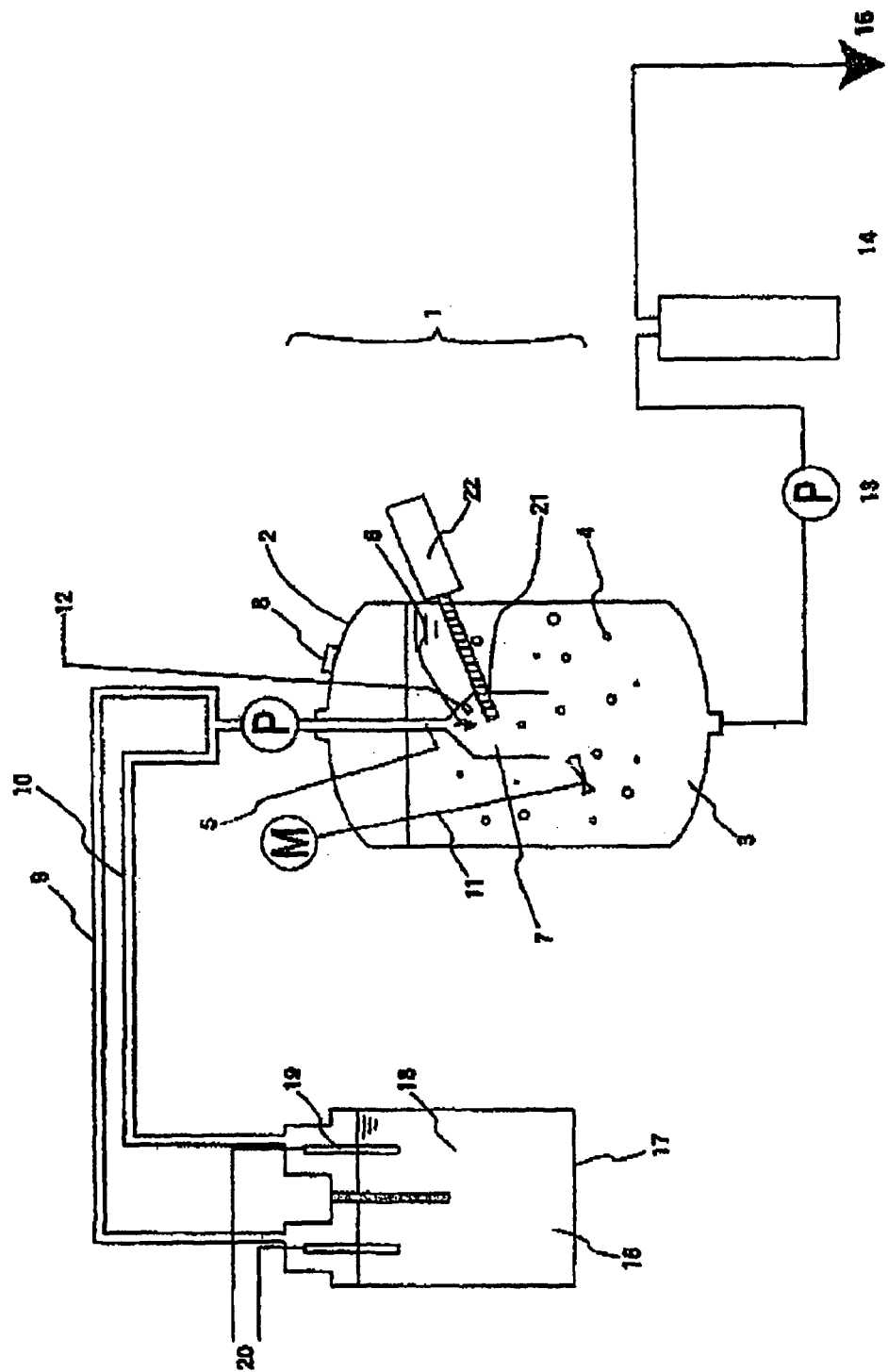

Production of fiber treatment agent:
"FIG. 2" shows a representative example of apparatus for producing treatment agent as proposed by the present invention. This apparatus (1) comprises a high-pressure tank (2), an injection nozzle for hydrogen and oxygen mixture gas (5), and a combustion chamber for mixture gas (7), and implements the method for producing dispersion water in which super-fine noble metal particles are dissolved.

The specific action is as follows. The production container is a pressure-resistant tank (2) made of metal, or preferably steel, into which raw water for producing pressurized water (3) is fed through an inlet (8). At the same time, a bar of noble metal material (21) is inserted and the high-pressure water is agitated and mixed by an agitator (11) driven by an electric motor (M). A combustion chamber (7) is provided around the injection nozzle (5) for the hydrogen and oxygen mixture gas (6) fed from a hydrogen feed line (9) and an oxygen feed line (10), and the mixture gas is ignited by an ignition plug (12) and burned completely to achieve a state of complete steam gas combustion at ultra-high temperature. This combustion gas instantly melts the noble metal, and consequently dispersion water in which super-fine noble metal particles are partially dissolved is produced. The dispersion water is fed by a pump (13) through a filter housing (14) and delivered as product.

Conditions

Pressurized water: 1 ton of water    Pressure: 2 kg/m$^2$
Mixture gas: 5 L/sec, 3.5 atmospheres
Injection time: 2 hours
Noble metal fed: 50 g
Produced dispersion water: Approx. 1 ton The produced dispersion water was diluted to approximately twice the original volume using distilled water to obtain a fiber treatment agent as described in component (1) of the present invention.

EXAMPLE 2

Treatment using fiber treatment agent:

Ten adult males and females were instructed to wear an undergarment treated with dispersion water in which super-fine gold particles are dispersed, and its efficacies and effects on promoting health and curing disease were verified. The results are summarized in "Table 1." The efficacies and effects were verified in the same manner after washing the garment five times. (a: Immediately after treatment, b: after washing five times)

* The figures in the table indicate the numbers of persons among the 10 subjects who felt that the undergarment was effective.

Comparison example: The subjects wore an undergarment treated with mineral water containing magnetic components.

TABLE 1

|  | The present invention | | Comparison example | |
|---|---|---|---|---|
| Evaluated undergarment | a | b | a | b |
| Promotion of perspiration | 8 | 6 | 2 | 0 |
| Enhancement of stamina | 7 | 5 | 0 | 0 |
| Increase in appetite | 3 | 3 | 0 | 0 |

TABLE 1-continued

|  | The present invention | | Comparison example | |
|---|---|---|---|---|
| Evaluated undergarment | a | b | a | b |
| Relief of fatigue | 8 | 8 | 1 | 0 |
| Lowering of high blood pressure | 3 | 3 | 0 | 0 |
| Increase in energy level | 4 | 4 | 2 | 1 |
| Curing of skin disease | 2 | 1 | 0 | 0 |

According to the above results, the undergarment treated with the fiber treatment agent proposed by the present invention showed remarkable efficacies and effects in promoting health and Curing disease, while the undergarment treated with commercially available mineral water containing magnetic components, which are considered health materials, showed little effects. Additionally, while the function of the undergarment obtained through the present invention remained relatively intact after repeated washings, the comparison product resulted in a further drop in its function.

INDUSTRIAL FIELD OF APPLICATION

As explained in details and described by examples above, the present invention provides a fiber treatment agent utilizing a newly developed method for producing dispersion water of super-fine noble metal particles, and the fiber products treated with the agent deliver remarkable effects on promoting health and curing disease as a result of the bioactive action of super-fine noble metal particles. This fiber treatment agent is also resistant to repeated washings and is therefore suitable for practical use.

What is claimed is:

1. A fiber treatment agent comprising micro-dispersion water consisting of super-fine noble metal particles as particles dispersed therein, said super-fine noble metal particles having a strong hydrophobic property and having a size on the order of $10^{-6}$–$10^{-9}$ m.

2. The fiber treatment agent as described in claim 1, wherein the super-fine noble metal particles are made of gold, silver or platinum.

3. The fiber treatment agent as described in claim 1, wherein the super-fine noble metal particles are made of gold.

* * * * *